United States Patent [19]

DiPoto et al.

[11] Patent Number: 5,258,016
[45] Date of Patent: Nov. 2, 1993

[54] SUTURE ANCHOR AND DRIVER ASSEMBLY

[75] Inventors: Gene P. DiPoto, Cumberland, R.I.; Jeffrey C. Cerier, Franklin, Mass.; Russell F. Warren, Greenwich, Conn.; Gerard S. Carlozzi, Weymouth; Paul DiCarlo, E. Falmouth, both of Mass.; James W. Dwyer, Brookfield, Conn.; Alan A. Small, Needham, Mass.

[73] Assignee: American Cyanamid Company, Stamford, Conn.

[21] Appl. No.: 836,679

[22] Filed: Feb. 14, 1992

Related U.S. Application Data

[63] Continuation-in-part of Ser. No. 681,042, Apr. 5, 1991, abandoned, which is a continuation-in-part of Ser. No. 552,440, Jul. 13, 1990, Pat. No. 5,100,417.

[51] Int. Cl.⁵ .............................................. A61B 17/60
[52] U.S. Cl. ...................... 606/232; 606/72; 606/74; 606/75; 606/104
[58] Field of Search .............. 606/232, 220, 236, 104, 606/73, 170, 139, 232, 72-75, 104

[56] References Cited

U.S. PATENT DOCUMENTS

| | | | |
|---|---|---|---|
| 2,329,398 | 9/1943 | Duffy | 604/104 |
| 3,003,155 | 10/1961 | Meilzynski et al. | 3/1 |
| 3,845,772 | 11/1974 | Smith | 128/335 |
| 4,409,974 | 10/1983 | Freedland | 128/92 |
| 4,454,875 | 6/1984 | Pratt et al. | 128/92 |
| 4,496,468 | 1/1985 | Li | 606/232 |
| 4,532,926 | 8/1985 | O'Holla | 128/334 |
| 4,632,100 | 12/1986 | Somers et al. | 606/73 |
| 4,653,486 | 3/1987 | Coker | 128/92 |
| 4,738,255 | 4/1988 | Goble et al. | 606/86 |
| 4,776,328 | 10/1988 | Frey et al. | 128/92 |
| 4,895,148 | 1/1990 | Bays et al. | 606/213 |
| 4,968,315 | 11/1990 | Gatturna | 606/72 |
| 5,002,550 | 3/1991 | Li | 606/139 |
| 5,019,080 | 5/1991 | Hemer | 606/104 |
| 5,037,422 | 8/1991 | Hayhurst et al. | 606/72 |

FOREIGN PATENT DOCUMENTS

| | | |
|---|---|---|
| 0260970 | 3/1988 | European Pat. Off. . |
| 2606270 | 5/1988 | France . |
| WO89/01767 | 3/1989 | PCT Int'l Appl. . |
| WO89/10096 | 11/1989 | PCT Int'l Appl. . |

OTHER PUBLICATIONS

Russell Warren, M.D., Technique for Using the Tag Tissue Anchor—Rod Style, Published Jul. 16, 1990.
John O. Hayhurst, M.D., Technique for Using the Tag Tissue Anchor—Wedge Style, Published Jul. 16, 1990.
Arthrex Brochure—"Arthrex ESP System: Expanding Suture Plug"—Feb., 1991? [Published prior to Mar. 1, 1991].

Primary Examiner—Stephen C. Pellegrino
Assistant Examiner—Gary Jackson
Attorney, Agent, or Firm—Douglas E. Denninger

[57] ABSTRACT

A suture anchor and anchor driver device for securely and accurately positioning and installing the suture anchor in place. The anchor has a rounded or pointed head and one or more ridges around it to help force fit the anchor into a hole and to hold it in place. A suture is positioned through the anchor for subsequent use during the surgical procedure. The driver device has a handle and an elongated shaft and is used to position and install the anchor in place. The anchor preferably snap fits onto the end of the shaft. A depth guide can be integrally or removably positioned on the shaft to ensure correct depth of placement. Alternately, the driver shaft is hollow and the anchor is positioned inside it and is implanted with a pusher member. The ends of the suture are affixed to the driver handle. Grooves can be provided on the driver and the anchor to prevent the suture from interfering with the positioning and installation procedure.

26 Claims, 9 Drawing Sheets

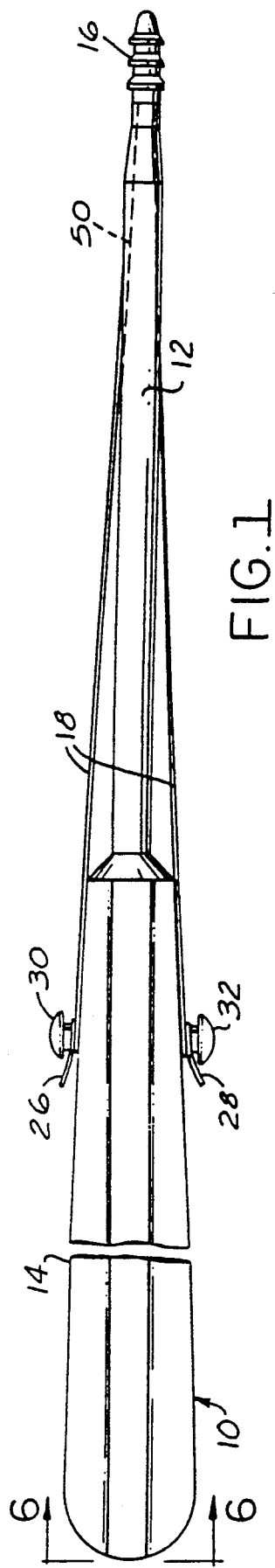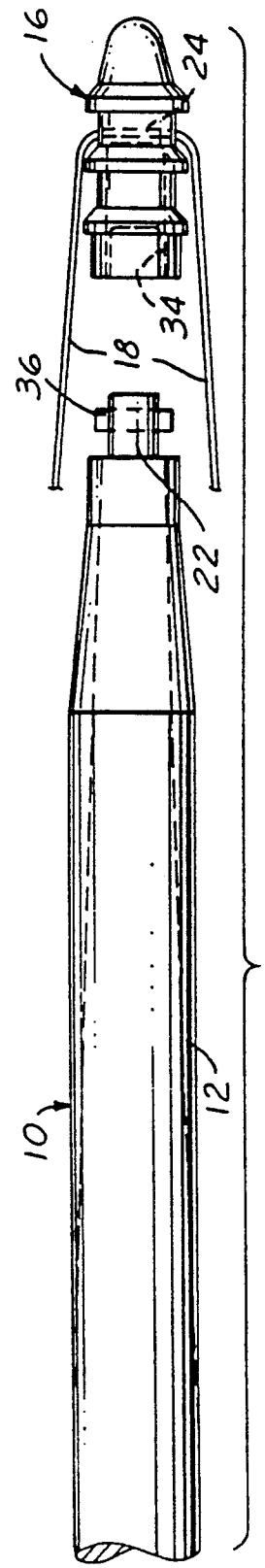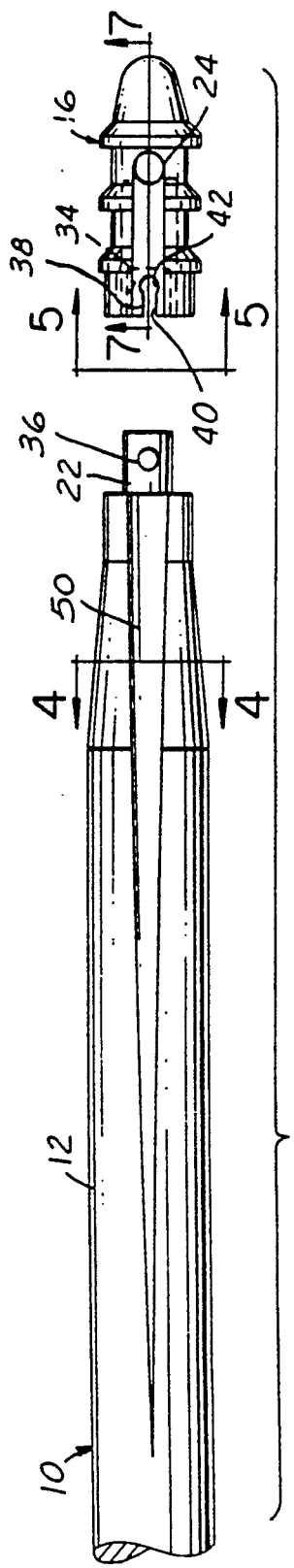
FIG.1
FIG.2
FIG.3

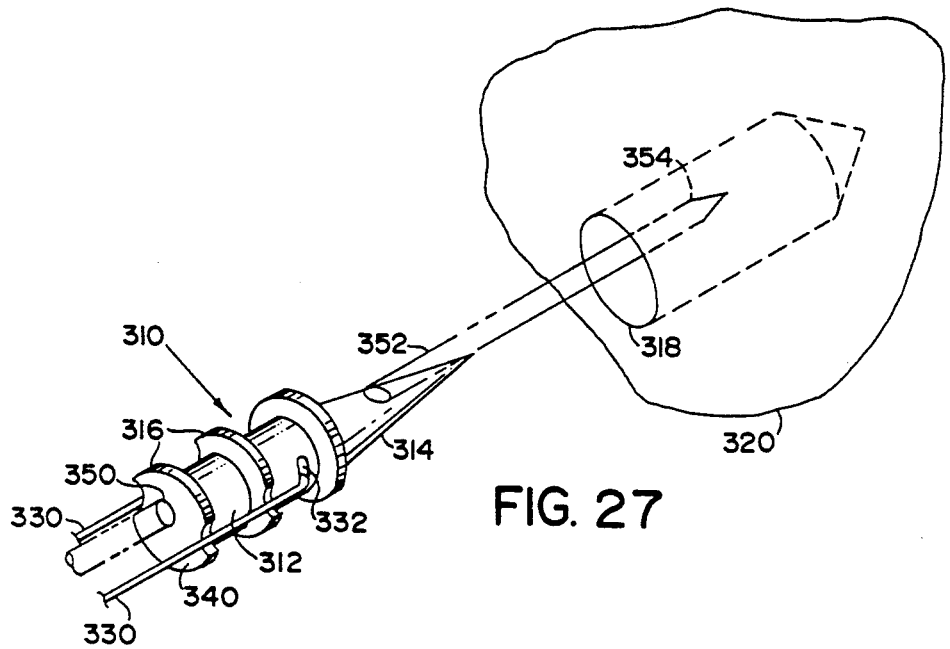
FIG. 27
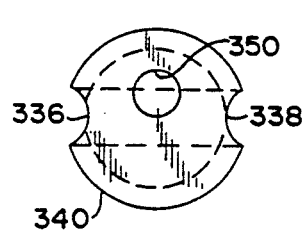
FIG. 28
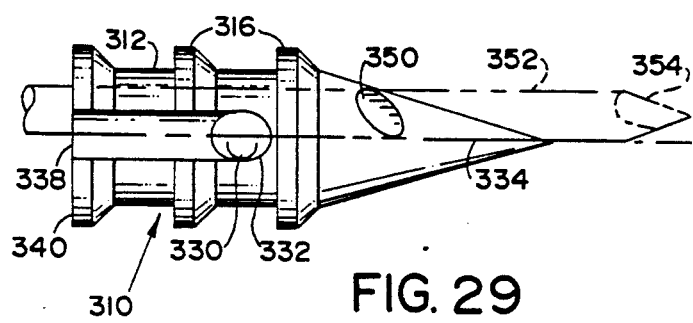
FIG. 29
FIG. 30
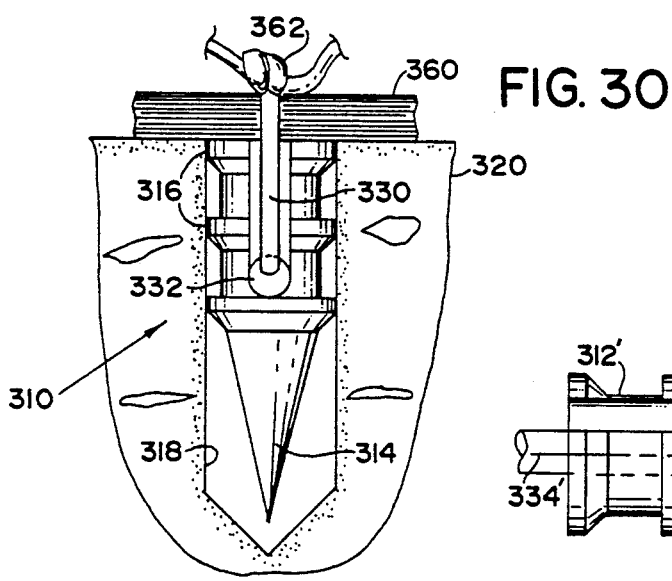
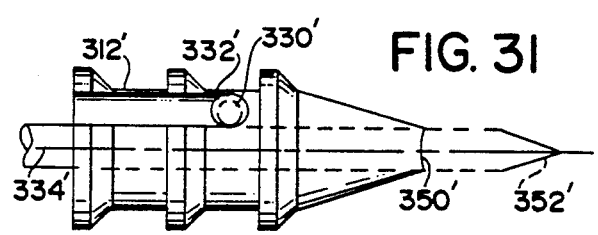
FIG. 31

SUTURE ANCHOR AND DRIVER ASSEMBLY

CROSS REFERENCE

This is a continuation-in-part of application Ser. No. 07/681,042, filed Apr. 5, 1991, now abandoned, which is a continuation-in-part of application Ser. No. 07/552,440, filed on Jul. 13, 1990, now U.S. Pat. No. 5,100,417.

FIELD OF THE INVENTION

A suture anchor for implanting in bone or tissue for surgical use is disclosed. The anchor is releasably engagable with the end of a driver device for reliable positioning and installation during surgery.

BACKGROUND OF THE INVENTION

Anchoring or affixation devices and systems for medical or surgical applications are in common use today. The anchors are implanted to aid in holding bone, tissue, ligaments and the like together or in place until healing takes place, or are used temporarily to help perform a procedure necessary for optimum surgical results. When implanted permanently, the anchors can be made from an absorbable material if desired.

Bone and suture anchors are used, for example, during orthopedic surgery to hold fractured bones together, to affix ligaments to bones and to aid in determining isometric placement of anterior cruciate ligament replacements. Examples of such anchors are shown in U.S. Pat. Nos. 4,537,185, 4,632,100, 4,640,271, 4,723,541 and 4,738,255.

Some positioning and driver mechanisms and systems are known which are used to accurately position and install bone anchors in place. Examples of such mechanisms and systems are disclosed, for example, in U.S. Pat. Nos. 3,990,438, 4,537,185, 4,632,100, 4,723,541 and 4,738,255. Two other known systems are the "Statak" mechanism marketed by Zimmer, Inc., Warsaw, Indiana and the "Isotac" mechanism marketed by Acufex Microsurgical, Inc., Mansfield, Mass.

SUMMARY OF THE INVENTION

It is an object of the present invention to provide an improved suture anchor for surgical use. It is another object of the present invention to provide an improved driver device for a suture anchor.

Yet another object of the present invention is to provide a suture anchor which readily and reliably attaches and detaches from a driver.

A further object of the present invention is to provide such a suture anchor which carries a simple yet strong attachment element for engaging the driver.

A further object of the invention is to provide such a suture anchor which maintains a desired alignment with the driver during insertion.

It is a still further object of the invention to provide a surgical anchor and driver assembly which allows efficient and accurate positioning and placement of the suture anchor during surgery, the anchor being able to be affixed either for permanent or temporary use, and the driver being able to remove the installed anchor if desired.

It is also an object of the invention to provide an anchor and driver assembly in which the suture anchor can be temporarily securely affixed to the driver device for installation and removal, and be removed easily from the driver device when desired. It is another object to provide means on the driver device to hold the anchor temporarily in place and prevent it from rotating relative to the driver device.

It is still another object to provide a surgical suture anchor and driver assembly in which a suture can be used to hold the anchor in place, the suture being recessed or positioned in a way not to obstruct or cause a problem during positioning, installation and/or removal of the anchor.

Another object of the invention is to provide a guide member for determining and limiting the depth of insertion of the anchor in the bone.

These and other objects are met by the present invention which will become apparent upon review of the following detailed description of the invention, when taken by itself or in view of the drawings.

The present invention relates to a unique and improved anchor, an anchor driver device, and a combined anchor and driver assembly. The anchor is a suture anchor with a rounded, conical or pointed tip which assists installation of the anchor into a previously drilled hole in bone or tissue. One or more ridges around its circumference act to hold the anchor in position in the hole for its intended use. Preferably, a suture is positioned through a hole in the anchor and extends from the anchor for subsequent use by the surgeon to hold ligaments, bones or tissue in place, or for use during isometric testing of the positioning for a substitute anterior cruciate ligament, for example.

The anchor is adapted to be securely positioned on the end of a driver device. The driver has a handle and elongated shaft. The anchor snaps or force fits onto the end of the shaft and is keyed against rotation. A guide member, which can be integral with the shaft, can be used to ensure correct depth of placement of the anchor and protect the sutures during use. The suture is affixed to the handle of the driver and grooves or slots may be provided along the driver shaft for positioning of the sutures during use of the anchor and driver assembly. By positioning the sutures in the grooves, they are placed out of the way so they cannot interfere with positioning, placement, installation or removal of the anchor.

In an alternative embodiment, the anchor is hollow and the driver handle and shaft are cannulated. This allows the sutures to be passed through the anchor and driver and not interfere with the installation or removal procedures. In yet another embodiment, the anchor and driver cannulated to receive a guide wire.

In another alternate embodiment, the driver device is also hollow and the anchor members are sized to fit inside of it. A pusher member is used to push the anchor member out of the driver and insert it into the bone or bone-like structure.

BRIEF DESCRIPTION OF DRAWINGS

FIG. 1 illustrates a unique anchor and driver assembly with the anchor being positioned and held in place on the driver;

FIG. 2 is a partial exploded view of the anchor and the end of the driver illustrating their features and showing how they are affixed together;

FIG. 3 is a partial exploded view similar to FIG. 2 but with the anchor and driver shaft rotated 90° relative to the view shown in FIG. 2 and with the suture removed for ease of viewing;

FIG. 27 is a perspective view of a cannulated anchor according to the present invention and a method for its installation;

FIGS. 28 and 29 are end and side elevational views of the cannulated anchor;

FIG. 30 depicts use of the cannulated anchor after it is installed; and

FIG. 31 depicts an alternate embodiment of a cannulated anchor.

DETAILED DESCRIPTION OF INVENTION

Figure 4:
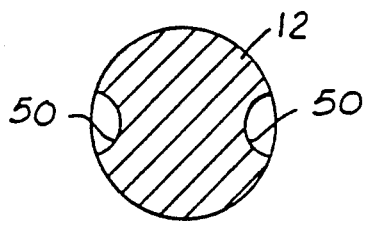
FIG. 4 is a cross-sectional view of the driver shaft taken along lines 4—4 in FIG. 3.

The features and details of one embodiment of a unique anchor and driver assembly are shown in FIGS. 1-7. The driver device is generally designated by the reference numeral 10 and the anchor by the reference numeral 16.

The driver device has a shaft member 12 attached or connected to a handle member 14. The shaft member and handle member can be separate members securely fastened together or they can be made from a single piece of material. Preferably the handle is a hollow stainless tube member having the shape shown in FIGS. 1 and 6 and the shaft is a stainless steel rod which is soldered, welded or otherwise affixed in or to the handle.

Figure 10:
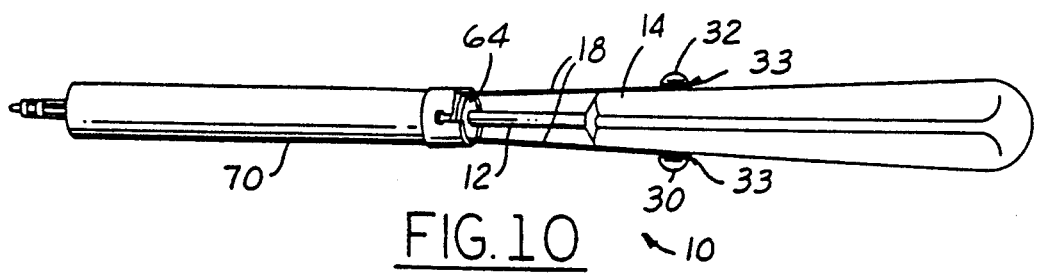
FIGS. 10, 10A and 11 illustrate the use of the inventive anchor and driver assembly with a separate depth guide member to install an anchor into a hole drilled in bone.

The anchor 16 is situated for installation (and also for removal if that is desired) on end projection 22, FIGS. 2 and 3, of the shaft 12, in a manner to be described in more detail below. A suture 18 is positioned through a hole or opening 24 in the anchor 16 and the two ends 26 and 28 of the suture are securely wrapped or tied around fixation posts 30 and 32, respectively, FIG. 1. In order to securely hold the sutures which are wrapped on the posts 30 and 32, O-rings preferably are positioned on the stems of each of the posts. (O-rings 33 are shown in FIG. 10.)

The positioning of the anchor 16 on end 22 and the affixation of the suture 18 on the fixation posts 30, 32 tightly and securely holds the anchor on the driver for use during surgery. In this manner, the anchor will not be subject to being dislodged, moved out of position on the shaft or accidentally displaced from the shaft while the driver is being used to position and place the anchor during surgery. This is particularly important when the anchor is being used during arthroscopic knee, shoulder or other joint surgery and it would be harmful for the anchor to become loose in the joint.

Figure 5:
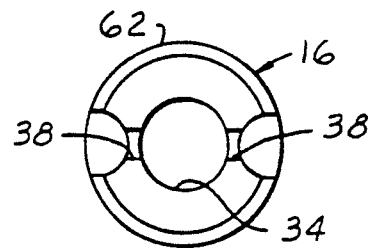
FIG. 5 is an end plan view of the anchor viewed along lines 5—5 in FIG. 3.
Figure 6:
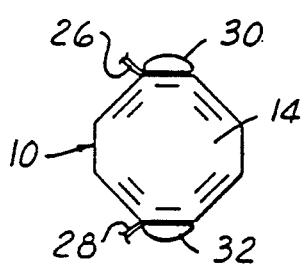
FIG. 6 is an end plan view of the driver device viewed along lines 6—6 in FIG. 1.
Figure 7:
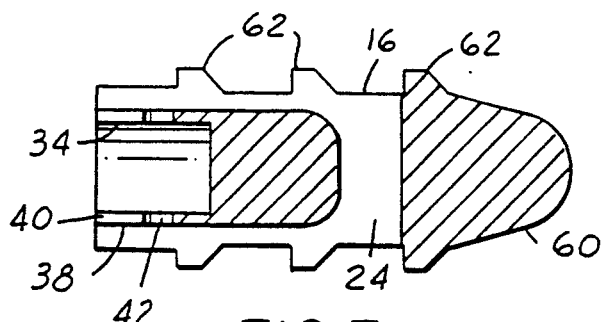
FIG. 7 is a cross-sectional view of the anchor taken along lines 7—7 in FIG. 3.

The end projection 22 is adapted to fit within a mating recess or socket 34 in the anchor 16, as shown in FIGS. 2, 3 and 5. The cross-sectional size and shape of the projection 22 and socket 34 can be of any common geometric shape, but preferably have the same shape and are circular, as shown by FIG. 5. If desired, the outside diameter of projection 22 and the inside diameter of socket 34 also can be dimensioned such that the two members have a frictional or slight force fit relationship.

A dowel or pin 36 is positioned in end projection 22 substantially perpendicular to the longitudinal axis of the driver device. The pin 36 projects on both sides of the end 22 forming two "ears" or "tabs".

The rod-type anchor 16 has a pair of slots 38 which are formed on opposite sides (180° apart) of the end of the anchor which fits on the driver device. The slots 38 are positioned and dimensioned to snap over and onto the protruding ends of the pin 36 on the driver. The slots 38 have an elongated passageway 40 which is slightly smaller in width than the cross-sectional diameter of the pin 36 and a larger generally circular end portion 42 which has substantially the same diameter as the pin 36.

The pin 36 "keys" the anchor to the shaft and driver so that the anchor cannot be rotated relative to the driver; the pin insures that the anchor can be rotated and maneuvered only with the driver.

The dimensioning of the slots 38 relative to the pin 36 also creates a force fit mating relationship and assembly between the anchor and driver device. The anchor 16 has to be forced onto the end 22 of the shaft by forcing the two ends of the pin 36 through the passageways 40 and into the openings 42. The anchor is resilient and "snaps" into place with the openings 42 on the shaft 36. This frictional or force-fit relationship also helps insure that the anchor and driver device will remain together during positioning and installation of the anchor during surgery.

The anchor in one construction made from a polyacetal such as Delrin 150SA material, but it can be made of any other equivalent or compatible plastic or surgical material. It is also possible for some applications for the anchor to be made of a bio-absorbable material, such as polyglycolic acid (PGA) or polylactic acid (PLA). U.S. Pat. Nos. 3,739,773 (Schmitt et al.), 4,300,565 (Rosensaft et al.) and 4,429,080 (Casey et al.) are incorporated herein by reference for their disclosure of bioabsorbable material.

One suture to be utilized with the present invention is No. USP Size 2 Ticron material made by Davis & Geck Co. It is understood, of course, that any other equivalent suture or other material can be used so long as it satisfies the purposes and objects of the present invention.

The suture 18 can be placed through the hole in the anchor 16 before or after the anchor is positioned on the end of the driver shaft.

A pair of elongated slots or grooves 50, FIGS. 3 and 4, are provided on the shaft 12. The grooves are positioned 180° apart on the shaft and are of sufficient size and depth to position and retain the suture 18. The grooves 50 are oriented on the driver in axial alignment with the protruding ends of the pin 36 and with the fixation posts 30 and 32. When the anchor 16 is positioned on the driver 10, the suture 18 is tightly pulled into the grooves 50, down the length of the shaft 18 and securely wrapped and affixed around the posts 30 and 32. The ends 26 and 28 of the suture 18 are wound tightly around the fixation posts 30 and 32 which helps to hold the anchor on the driver during use.

After the anchor is positioned and installed in place, the ends of the suture are released from the posts 30 and 32 and the driver is pulled from the site. The fixation of the anchor 16 in the bone or tissue must be sufficiently strong and secure to allow the post 36 to be removed from the slots 38. Once the driver device is removed, the anchor 16 and suture 18 attached thereto are positioned in place for subsequent use during surgery. One such use is to fasten the end of a substitute or synthetic ACL ligament. In general, the anchor can be utilized to attach or reattach soft tissue, ligaments and tendons to bone. In these applications, the anchor would remain permanently in place. Another such use is the isometric testing of a proposed position for installation of an ACL replacement. In this application, the anchor and suture would be removed (and discarded) after the isometric testing was completed. In order to remove the anchor 16, the driver device is again utilized and the installation process reversed.

The shape and configuration of the anchor 16 is best shown in FIGS. 2, 3, 5 and 7. The anchor has a front end or tip 60 which is rounded, conical or pointed for ease of placement and insertion. A sharp pointed anchor would allow it to pierce soft tissue more easily. A plurality of circular ridges 62 extend around the circumference of the anchor and are used to firmly and securely hold the anchor 16 in place in a hole.

When the hole for the anchor 16 is drilled or formed in the bone or tissue, the diameter of the drill should be slightly less than the outer diameter of the ridges 62. In this manner, the anchor 16 can be forced into position in the hole and the compression and friction caused by the ridges 62 against the inner walls of the hole will hold it firmly in place.

Preferably the outer diameter of the ridges is 0.169 inches and the length of the anchor is 0.410 inches. The socket 34 has a diameter of 0.078 inches and a depth of 0.100 inches. The diameter of the end projection 22 is preferably 0.076–0.077 inches and the length of the pin 36 is 0.097 inches. The passageway of the slots 38 has a width of 0.025 inches and the pin 36 has a diameter of 0.0313 inches. The overall length of the driver device 10 (handle and shaft) is approximately 10 inches. Other sizes and dimensions for the present invention can also be utilized.

Three ridges 62 are shown on the anchor 16 and utilized in the preferred embodiment for sufficient strength of the anchor and to provide the requisite holding force in the bone or tissue. It is understood, of course, that a greater or lesser number of ridges could be provided in accordance with the present invention so long as the objects and purposes of the present invention are obtained.

After the hole in the bone or tissue is formed (by drilling, for example with a K-wire having a diameter of 0.146 inches), the anchor 16 is "snapped" into position on the end 22 of the shaft of the driver and the suture 1B tightly wound on the fixation posts. The anchor and driver assembly is then maneuvered or moved into position by the surgeon (e.g. arthroscopically), and the tip 60 of the anchor positioned at or in the opening of the hole. The anchor 16 is then forced axially into the hole by, for example, the surgeon tapping on the end of the driver with a mallet or the like. It is not necessary to rotate the assembly in order to install it in position.

Figure 8:
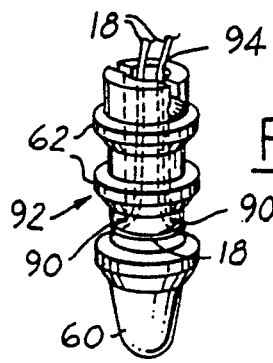
FIGS. 8 and 9 illustrate alternate embodiments of a hollow anchor and driver device.
Figure 9:
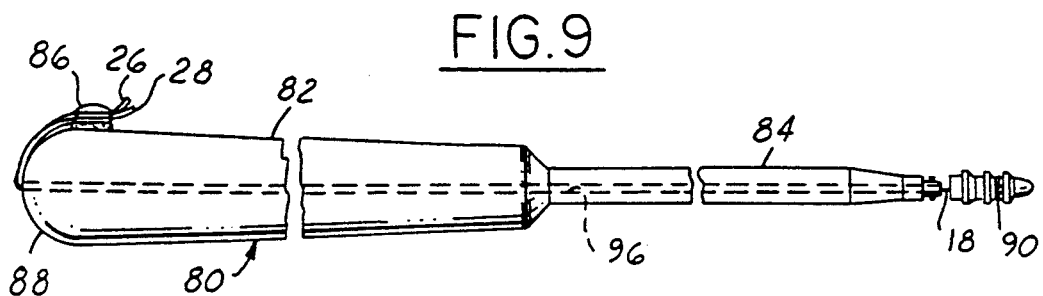

In an alternate embodiment, a driver device 80, FIGS. 8 and 9, having a handle 82 and shaft 84, is cannulated and the suture 18 is passed down the length of the driver and affixed on a fixation post 86 positioned adjacent the end 88 of the handle 82. The suture 18 is passed through opening 90 in a hollow anchor 92 and out through the open hollow interior 94 of the anchor 92. In this embodiment, a suture passer can be utilized to thread the suture through the passageway or channel 96 in the driver 80. The driver 80 and an attached anchor can be guided over a guide wire when the anchor defines a guide wire passage as described below for FIGS. 27–31.

Figure 10A:
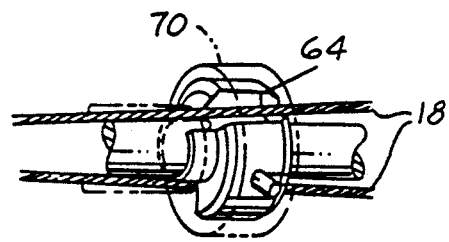
Figure 11:
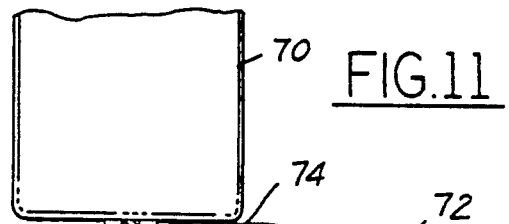

To avoid over-penetration of the anchor 16 into the bone, a guide member 70 is positioned over the shaft 12 of the driver instrument in one construction, as shown in FIG. 10. The guide member is a hollow cylindrical member, preferably made of plastic, and slips over the driver and anchor assembly after the anchor is positioned on the driver device and the ends of the suture 18 are attached to the fixation posts 30 and 32. Preferably, the guide member 70 is held in place on the driver instrument 10 by a stop or collar member 64 which is soldered to the shaft 12 (see FIG. 10A). The guide member 70 has a pair of opposed slots 66 which snap-fit over pins 68 on the stop member in order to hold it in place. The guide member also protects the sutures during use of the assembly during surgery. A series of guide members of different lengths can be provided in order to provide the insertion depth desired by the surgeon for the anchor. When the anchor is installed in the bone or bone-like structure 72, as shown in FIG. 11, the end 74 of the guide member 70 contacts the bone and prevents the anchor from being inserted too far into the bone.

Figure 12:
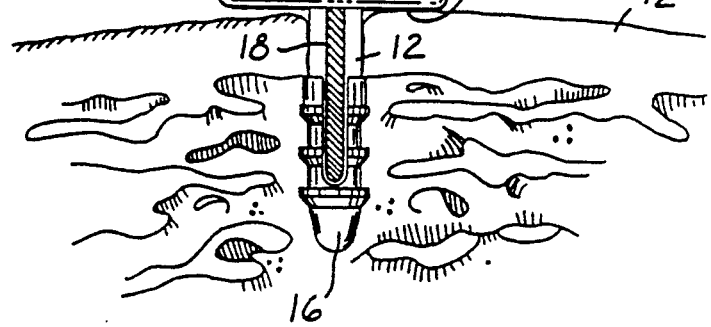
FIG. 12 illustrates the "setting" of the anchor in the drilled hole.
Figure 12:
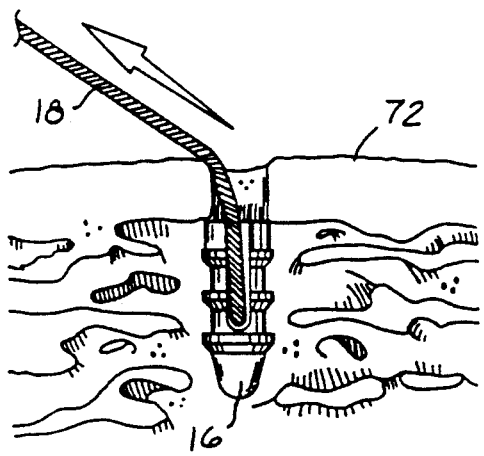
Figure 13:
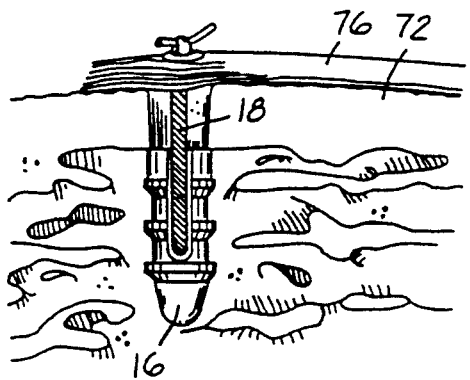
FIG. 13 illustrates the use of the invention to affix soft tissue to the bone.

Once the anchor is firmly set in place, the ends 26 and 28 of the suture 18 are removed (unwound) from the fixation posts 30 and 32 and the driver is removed from the surgical site. Since the anchor is retained in the hole with a greater force than that required to snap and unsnap the anchor from the pin 36 on the driver, the driver can be removed easily from the anchor by the surgeon. The two ends of the suture 18 preferably are pulled firmly at an angle to the bone 72, FIG. 12, to ensure a firm fit and more securely set the anchor in place. The anchor with suture attached is then used for its intended use. One such use is shown in FIG. 13 where the suture 18 is tied through a soft tissue (ligament) 76 securely fastening it to the bone 72. In this manner, the ligament is mechanically reattached to the bone and, over time, the two members grow together and become permanently biologically reattached.

If the anchor is to be removed after use, or moved to another position, the installation process is repeated in reverse order, as mentioned earlier.

Figure 14:
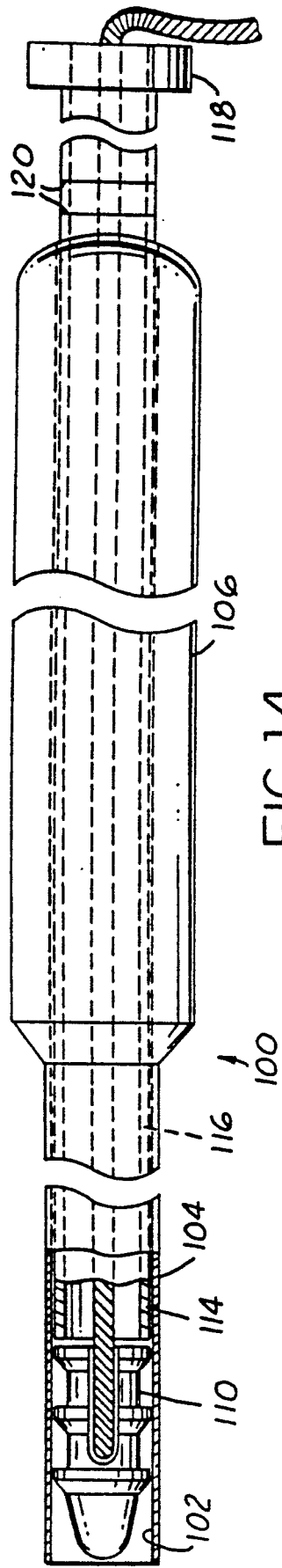
FIG. 14 illustrates another alternate embodiment of the invention.

In another embodiment, FIG. 14, the driver device 100 is hollow with a central opening 102 through the length of the elongated shaft 104 and handle 106. The anchor member 110 is sized sufficiently small to fit within the opening 102 and has a suture 112 attached to it, in the same manner as suture 18 is attached to anchor 16 as described above. A pusher member 114 consisting of an elongated tubular member 116 and head or handle 118 is inserted in the opening 102 and used to drive the anchor member 110 through and out of the driver device 100 and into the bone or bone-like structure. The suture 112 is threaded through the driver device and pusher member, as shown.

In order to gauge and measure the depth of insertion of the anchor member 110, markings or a scale 120 can be provided on the pusher member. The "hollow tube" driver device is particularly useful for insertion of small anchor member 110, such as on the order of about one-sixteenth of an inch in diameter and three-sixteenths of an inch in length.

Figure 15:
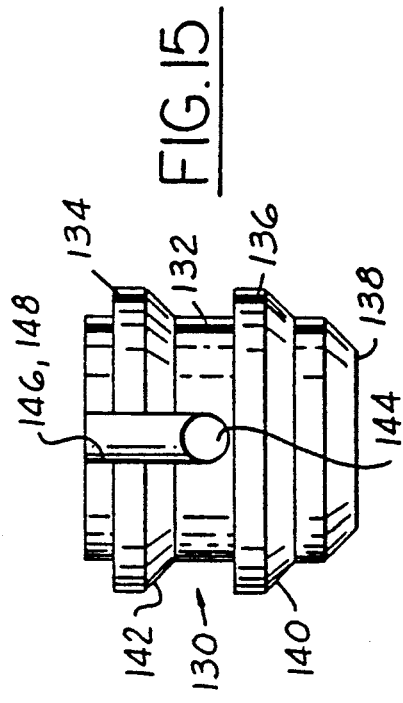
FIG. 15 depicts still another embodiment of a solid, rod-type anchor.
Figure 16:
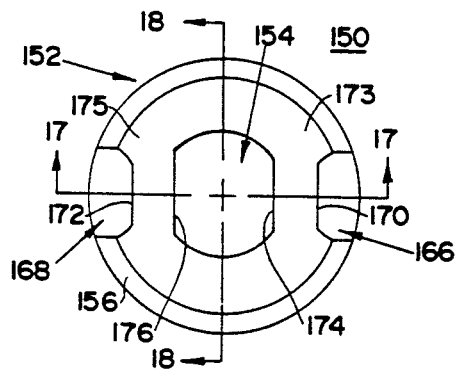
FIGS. 16A and 16B are proximal end views of alternative embodiments of anchors according to the present invention in which the anchors define intact sockets for engaging a driver.
Figure 16:
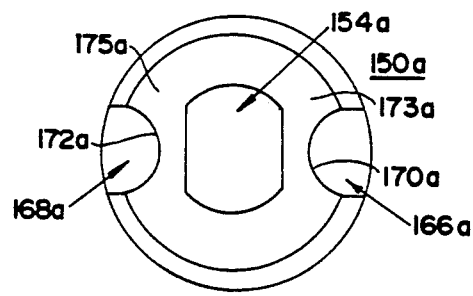

A solid anchor 130, FIG. 15, has a rodshaped body 132 with a pair of annular rings 134 and 136 on its outer surface. The front end 138 of the anchor is flat with a 45° chamfer around the edge in order to ease entry of the anchor into the hole in the bone. Chamfer or angled surfaces 140 and 142 are provided on the leading edges of the rings 134 and 136 also in order to ease entry of the anchor into the bone. A hole 144 with opposed slots 146 and 148 are provided for positioning of the suture.

Additional embodiments of suture anchors and drivers according to the present invention are shown in FIGS. 16A-26 in which the anchor has greater strength and structural integrity at the region of engagement with the driver. Anchor 150, FIGS. 16A, 17 and 18, includes an elongated body 152, a drive socket 154, first and second discontinuous, interrupted ridges 156, 158, and continuous, uninterrupted distal ridge 160. The anchor 150 further includes a rounded distal tip 162, and a suture passage 164. A pair of grooves 166, 168 are disposed on opposing sides of the anchor 150. The inner, proximal portions of the grooves 166, 168 are bounded by flat surfaces 170, 172.

A substantial wall thickness is thereby achieved for walls 173, 175 which lie between the grooved surfaces 170, 172 and the flat surfaces 174, 176 of the socket 154. The thickness and configuration of walls 173 and 175 provide increased resistance to initiation and propagation of fractures as compared with anchor 16, FIGS. 5–7.

By comparison, the grooves 166a, 168a of alternative anchor 150a, FIG. 16B, have rounded surfaces 170a, 172a which provide a deeper channel in which a thicker suture can be nestled. To maintain the same dimensions of the socket 154a as for socket 154, FIG. 16A, the walls 153a, 155a are thinner. When the anchor is to be constructed of a bioabsorbable material and is to be relatively small in size, the construction shown in FIG. 16A enables a stronger angled force to be applied to the anchor 150. The greater strength can be especially desired in surgical applications where anchor insertion cannot occur exactly perpendicular to the bone surface.

Figure 17:
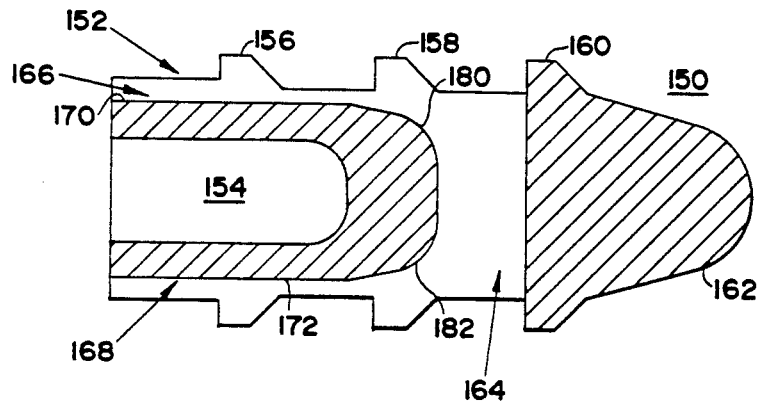
FIG. 17 is a longitudinal cross-sectional view along lines 17—17 of FIG. 16A

A gradual transition is made between the grooves 166, 168 and the transverse passage 164 by shoulders 180, 182 as shown in FIG. 17. Forces applied on a loaded suture, such as for suture 18 in FIGS. 12 and 13, are thereby distributed fairly uniformly over the areas of contact between the suture and the anchor.

Figure 19:
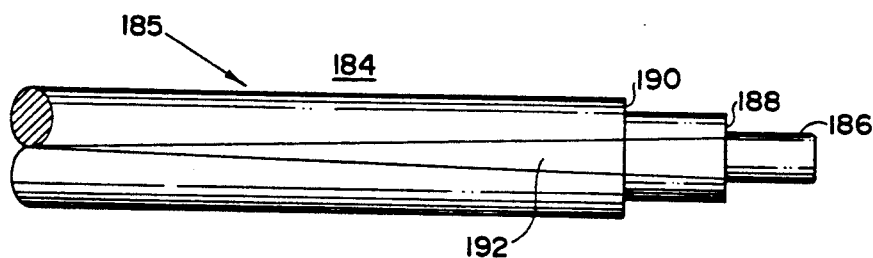
FIGS. 19 and 20 are different side views of a driver for engaging the anchors shown in FIGS. 16A, 17 and 18.
Figure 20:
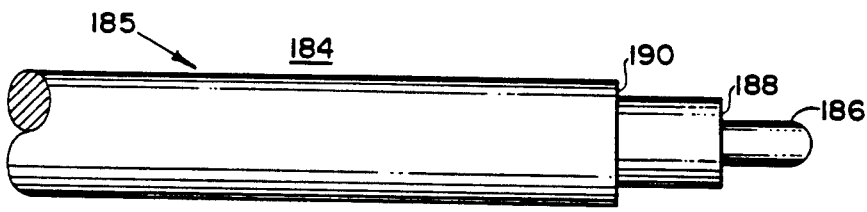
Figure 21:
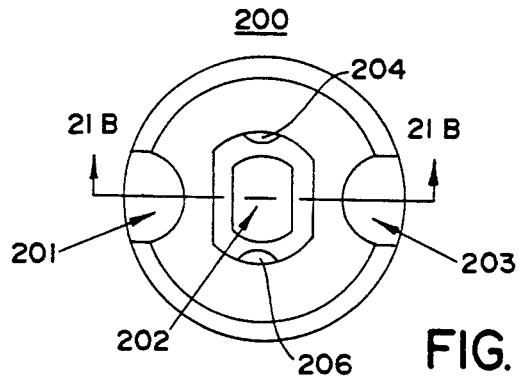
FIGS. 21A and 21B are end and cross-sectional views, respectively, of yet another anchor according to the present invention having a tapered drive socket.
Figure 21:
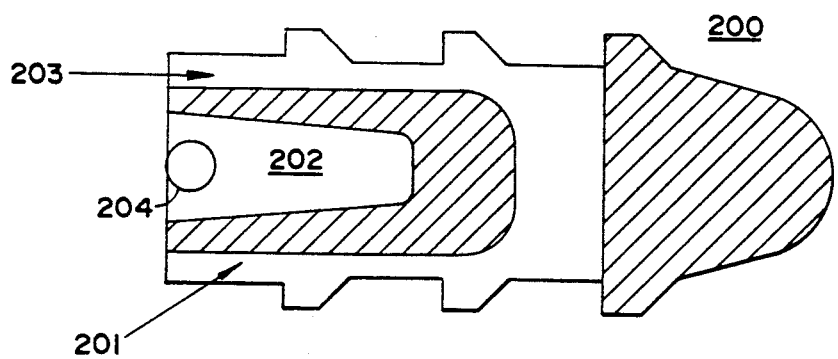
Figure 22:
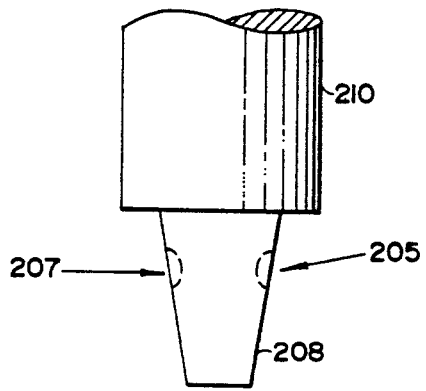
FIGS. 22A and 22B are partial side views of the distal ends of the drivers for engaging the anchor shown in FIG. 21.
Figure 22:
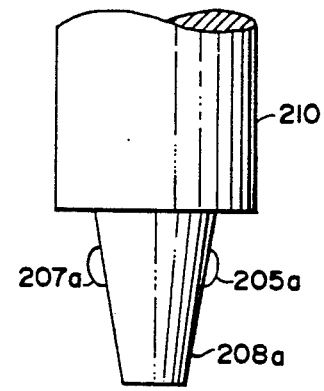

The distal portion of a driver 184, FIGS. 19 and 20, terminates in a drive element 186 which closely matches shape of the socket 154 of anchor 150. A shoulder 188 is formed proximally on the shaft 185 to engage the proximal end of the anchor 150. The shaft 185 further includes an integral depth stop 190 that is larger in diameter than the hole drilled in the bone and therefore acts as a depth guide to limit insertion of the anchor 150. The shaft 185 further defines a trough or slot 192 which increases in width and depth as it extends distally to the shoulder 188. A portion of the suture lies in slot 192 when the anchor 150 is secured to the driver 184 similar to the manner shown in FIG. 1, above.

Preferred dimensions for one construction of the anchor 150 and the driver 184 are as follows. The anchor 150 has an overall length of 0.41 inch and a maximum diameter of 0.148 inch at proximal region 177. The ridges 156, 158, 160 have a greater diameter of 0.169 inch. The socket 154 has a length of 0.15 inch, a minimum width of 0.064 inch and a maximum width of 0.078 inch. The socket 154 is therefore narrower in a first dimension as shown in FIG. 17 than along a second dimension as shown FIG. 18.

Figure 18:
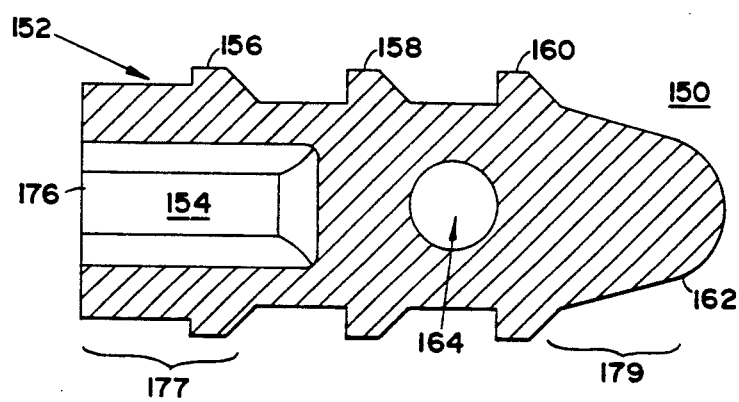
FIG. 18 is similar cross-sectional view along lines 18—18.

In this construction, the socket walls 173, 175 have a width of 0.023 inch and the passage 164, FIG. 18, has a minimum diameter of 0.056 inch. The grooves 166, 168 have a width of 0.055 inch and a depth of 0.029 inch. The distal region 179 has a maximum diameter of 0.128 which successively narrows progressing distally.

The driver 185, FIGS. 19 and 20, is 9.85 inch in length, and the shaft 185 has a diameter of 0.187 inch. The shoulder 188 has a diameter of 0.14 inch while the drive engagement element 186 has a width along the dimension shown in FIG. 19 of 0.077 inch and a width along the dimension shown in FIG. 20 of 0.067 inch. The latter width is slightly larger than the corresponding width of the socket 154 which generates a friction or force-fit between the anchor 150 and the driver 185 to snugly attach the anchor to the driver. The non-circular cross-sections of the socket 154 and the driver element 186 ensure accurate alignment between the anchor grooves 166, 168 and the shaft slots 192 so that a suture can be nestled therein to avoid impingement with the bone or other tissue. The slot 192 has a maximum width of 0.053 inch and a depth of 0.028 inch at shoulder 188 in this construction, and exhibits a slope of approximately two degrees.

Anchor 200, FIGS. 21A and 21B, is similar to anchor 150 but defines a socket 202 which becomes narrower progressing distally to provide greater overall strength for the anchor 200 by allowing thicker distal walls. The socket 202 progresses from proximal dimensions of 0.078 inch by 0.064 inch distally to cross-sectional dimensions of 0.050 inch by 0.040 inch. The distal taper of the socket 202 also enables deeper suture grooves 201, 203 without compromising the strength and integrity of the anchor 200.

The anchor 200 further includes projections 204, 206 which engage matching recesses 205, 207, FIG. 22A, of a driver engagement element 208. Driver shoulder 210 engages the proximal end of the driver 200 for insertion of the anchor as described above. The interlocking of the matching detents and recesses provide resistance to separation between the anchor and the driver in an alternative manner to the force-fit interlocking between driver element 186 and socket 154 described above.

Alternatively, projections 205a, 207a are located on the driver element 208a as shown FIG. 22B. Matching recesses are defined in the corresponding anchor.

Figure 23:
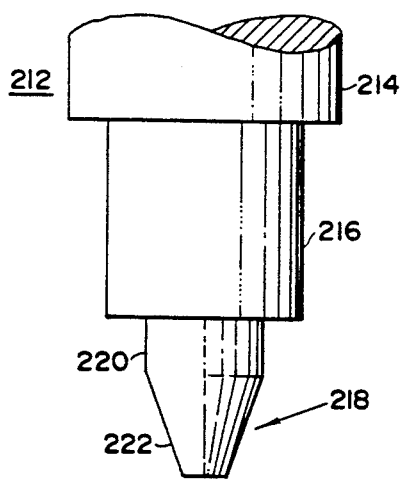
FIG. 23 is a similar side view showing a driver having an integral depth stop and an engagement tip which facilitates an interference or force-fit with the suture anchor.
Figure 24:
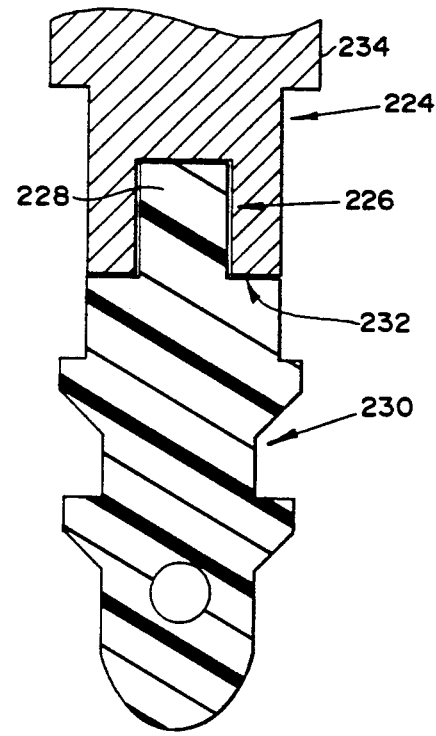
FIG. 24 is a cross-sectional view of yet another anchor and driver in which the anchor projects into a socket in the driver.

Two additional driver-to-anchor engagement arrangements are shown in FIGS. 23 and 24. A driver 212 includes an integral depth stop 214, a driver shoulder 216, and a drive element 218 having a proximal straight section 220 and a distal tapered section 222. The straight section 220 enables an interlocking force-fit with corresponding anchor while the distal tapered section 222 enables the more distal portions of the anchor to be thicker and therefore stronger.

A driver 224, FIG. 24, defines a distal socket 226 for engaging a projection 228 of an anchor 230. A distal surface 232 of the driver 224 serves as an engagement shoulder for transferring force to the proximal end of the anchor 230. In one construction, the depth stop 234 has a diameter of 0.185 inch, the shoulder 232 has an outer diameter of 0.14 inch and socket 226 has a diameter ranging from 0.06 to 0.1 inch.

While most of the anchors described above have rounded, bullet-shaped distal tips, this is not a limitation of the invention. Other tip configurations include frustoconical geometries and other shapes preferably having a successively narrowing cross-section proceeding distally to facilitate insertion into a previously drilled hole.

Figure 25:
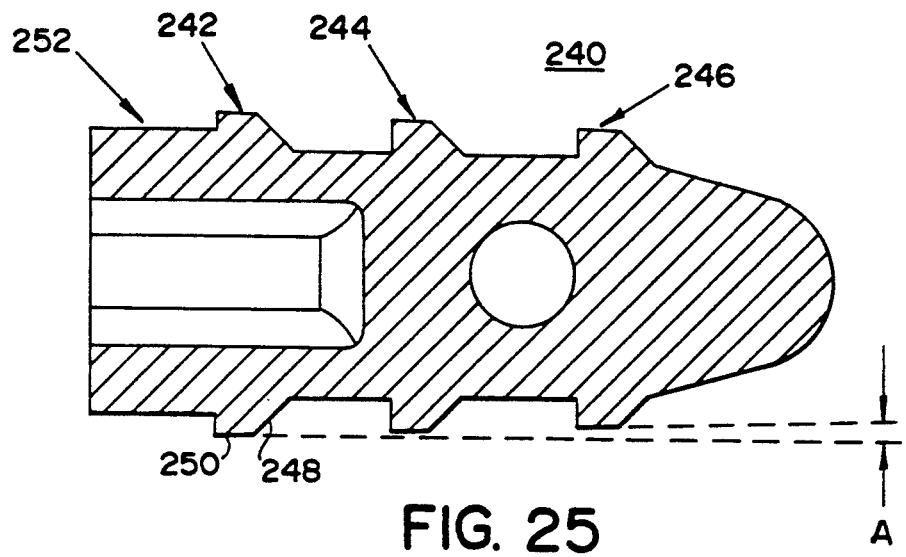
FIGS. 25 and 26 are cross-sectional views of other anchors having tapered and stepped ridges, respectively.
Figure 26:
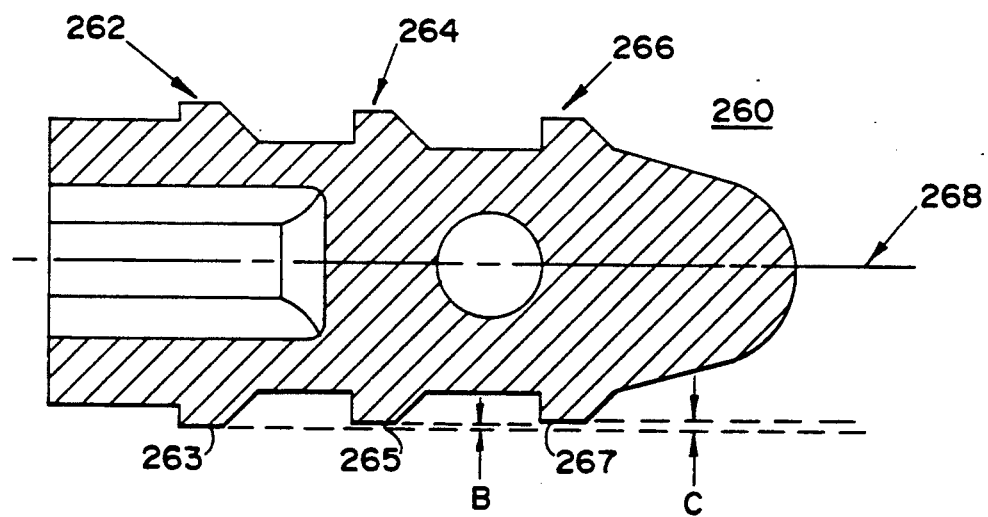

Additional variations within the scope of the present invention include two or more ridges of different diameters as shown in FIGS. 25 and 26. Anchor 240 includes a proximal ridge 242 having a diameter of 0.169 inch, an intermediate ridge 244 having a diameter of 0.157 inch, and a distal ridge 246 having a maximum diameter of 0.145 inch. Each ridge defines an inclined leading surface 248 and an outer bone engagement surface 250. In this construction, the surfaces 250 of the ridges 242, 244 and 246 are tapered at an angle A of up to ten degrees, more preferably at five to seven degrees.

Preferably, the resulting outer diameter of the distal ridge 246 is the same or slightly greater than the diameter of a hole drilled in bone into which the anchor 240 is to be inserted. The successively decreasing diameters of the ridges in the distal direction decreases the insertion force required to implant the anchors while retaining high-pull out resistance, especially as provided by the more proximal, greater-diameter ridges. Additionally, the proximal region 252 can have the same or slightly greater diameter than the drilled hole to enhance frictional engagement with the bone hole.

Decreasing diameter as provided by stepped ridges is shown for anchor 260 in FIG. 26. Ridges 262, 264, 266 have outer, bone engaging surfaces 263, 265, 267 which are parallel to the longitudinal axis 268 but are of decreasing, stepped diameter progressing distally. In one construction, the intermediate ridge 264 has a radial difference B of 0.006 inch relative to the proximal ridge 262 and the distal ridge 266 has a radial difference C of 0.012 inch to facilitate insertion into the bone. In addition to providing an increased surface area for engagement with bone, the non-triangular profile of the ridges provides increased strength and minimizes shear of the ridges.

A suture anchor in accordance with the present invention can also be cannulated as indicated generally by the reference numeral 310 in FIGS. 27–30. The anchor 310 has a generally cylindrical body 312 with a pointed leading end 314. The end 314 can be rounded, conical or pointed and is angled to assist the entrance and positioning of the anchor in a bone hole. Preferably, the leading end 314 is shaped to "blend" into the guide wire when it projects through the anchor 310.

The body 312 has a plurality of ridges 316 on its outer surface. The ridges help affix the anchor in position in a hole 318 in a bone 320. The ridges are sized slightly larger than the diameter of the hole to provide an interference or force-fit relationship. It is understood that the ridges can have a conventional shape and can consist of barbs or other structures provided for the same locking purpose.

A suture 330 is attached to the anchor 310. The suture is positioned through a hole or passageway 332 which is located generally transverse to the longitudinal axis 334 of the anchor. A pair of opposed channels 336, 338 extend from the hole 332 to the end 340 of the body 312. The channels are provided for positioning and placement of the suture 330 when it is installed.

A longitudinal guide wire passageway 350 is provided throughout the length of the anchor 310. As shown in FIGS. 27–29, the passageway 350 is offset from the central longitudinal axis 334 of the anchor. In this manner, the suture 330 in the transverse suture passageway 332 will not block the insertion of a guide wire 352 or the like in the longitudinal passageway 350. Similarly, the guide wire 352 will not interfere or cause damage to the suture 330.

When the anchor 310 is installed, the suture 330 is positioned through passageway 332 as shown in FIG. 27. A hole 318 in the bone 320 is formed by any conventional means, such as by a surgical drill. The hole 318 is positioned at an appropriate site as determined by the surgeon. The diameter of the hole 318 is selected to allow the anchor 310 to be installed in an interference or force-fit relationship.

A guide wire 352 is inserted through passageway 350 in the anchor 310 and the tip 354 of the guide wire 352 is positioned in hole 318. The anchor 310 is then slid along the guide wire by a conventional means, such as by a pusher rod or ram and forced into the hole 318. Once the anchor is installed in position, the guide wire is removed. Alternatively, the guide wire 352 can first be installed in position in the hole 318 and the anchor 310 then inserted over the guide wire and pushed into position.

The proximal portion of the anchor 310 can alternatively define a driver interlocking element to accomplish one of the novel anchor-to-driver engagement mechanisms described above. The driver can be cannulated such as shown in FIG. 9 for driver 80. To avoid possible damage to the suture, a separate guide wire passageway can be provided in the driver 80. Alternatively, the suture can be separately passed along the outside of a shaft having an exterior as shown for driver 10, FIG. 1, or for driver 184, FIG. 19, while the shaft additionally defines a guide wire passageway.

Once the anchor 310 is installed, the suture 330 is used to secure a piece of body tissue 360 or the like to the bone 320 as shown in FIG. 30. The ends of the suture 330 are passed through the material 360 and tied into a knot 362 tightly securing the material in place.

The anchor 310 may be made of any conventional material commonly used today for suture anchors. It can also be made of either an absorbable or non-absorbable material. Preferred bioabsorbable materials include polyglycolic acid, polyactic acid, or trimethylene carbonate copolymers. Preferred non-bioabsorbable materials include acetal homopolymers or copolymers thereof.

The materials for the suture 330 can also be of any conventional type, and the materials can be either absorbable or non-absorbable. Conventional types of sutures which can be utilized are the "Ticron" and "Dexon" brand sutures available from Davis & Geck.

Cannulation of a suture anchor according to the present invention is particularly useful for installing small suture anchors in place. "Small" suture anchors are typically 4-6 mm in length and 2-4 mm in diameter. Suture anchors of this size are difficult to handle and accurately install. It is also important to prevent the small anchors from loosening or becoming dislodged in a joint of a patient where they could cause complications and require retrieval.

Prior to the present invention involving an offset guide wire channel, it was not possible to install small suture anchors over guide wires or positioning mechanisms. There was insufficient room in the anchor body for both a cannulated passageway required for installation purposes as well as the channel and slots needed to attach the suture to the anchor.

An alternate embodiment of a cannulated anchor according to the invention is shown in FIG. 31. A traverse suture passageway 332' of an anchor 310' is positioned offset from the direct intersection with the central longitudinal axis 334' while the longitudinal passageway 350' for the guide wire extends along the central axis. In this manner, the guide wire 352' and suture 330' also do not interfere with one another during installation of the anchor 310' because passageway 332' and 350' do not intersect.

Although particular embodiments of the present invention have been illustrated in the accompanying drawings and described in the foregoing detailed description, it is to be understood that the present invention is not to be limited to just the embodiments disclosed, but that they are capable of numerous rearrangements, modifications and substitutions without departing from the scope of the claims hereafter.

What is claimed is:

1. An anchor for securing a suture to a bone, comprising:
   an elongated body having a proximal region terminating in a proximal end, and a distal region with a successively narrower cross-section terminating in a distal end to facilitate insertion into a hole drilled in the bone;
   means, disposed in said proximal region, for engaging a driver for insertion of said anchor into the drilled hole;
   at least one ridge, disposed continuously about the exterior surface of said body, for engaging the bone after insertion to resist withdrawal of said anchor; and
   means, defined by said elongated body, for carrying a portion of the suture to hold the suture at a selected position in the bone;
   said means for carrying including a passage traversing said elongated body through which the portion of the suture is insertable; and
   said means for carrying further including a pair of grooves extending proximally from said passage to said proximal end of said elongated body.

2. The anchor of claim 1 in which said means for engaging includes means for interlocking with a corresponding element of the driver.

3. The anchor of claim 2 in which said means for interlocking includes a force-fit established between said means for engaging and the corresponding driver element.

4. The anchor of claim 1 in which said means for engaging includes a socket defined by said elongated body which has an opening communicating with said proximal end of said body.

5. The anchor of claim 1 in which said elongated body is substantially cylindrical.

6. The anchor of claim 1 in which said elongated body is substantially circular in cross-section to facilitate insertion into a round drilled hole having a lesser diameter than the outer diameter of said ridge.

7. The anchor of claim 1 in which said distal end is substantially rounded.

8. The anchor of claim 1 in which said ridge includes a bone engaging surface and an inclined leading surface which extends from said bone engaging surface distally and inwardly to said elongated body.

9. The anchor of claim 8 in which said bone engaging surface is substantially parallel to the longitudinal axis of said elongated body.

10. The anchor of claim 1 in which said passage is disposed between said means for engaging and said ridge.

11. The anchor of claim 1 in which said elongated body is formed of a polymer having sufficient resiliency to enable said means for engaging to form a force-fit engagement with the driver.

12. The anchor of claim 11 in which said polymer is bioabsorbable.

13. The anchor of claim 1 further including at least a second, discontinuous ridge disposed between said passage and said means for engaging.

14. An anchor for fastening a suture into a hole in a bone or bone-like structure, said anchor comprising:
   an elongated rod-like body member having a leading end and a trailing end;
   at least one annular ridge substantially surrounding and forming a ring around the periphery of said body member;
   said annular ridge having a substantially flat outer surface;
   an opening through said body member adjacent said leading end; and
   a pair of opposed grooves in said body member extending from said opening to said trailing end.

15. The anchor of claim 14 in which said opening is adapted to carry a portion of the suture to hold the suture at a selected position in the bone.

16. The anchor of claim 14 further including means, disposed in said trailing end, for engaging a driver for insertion of said anchor into the hole.

17. An anchor and driver assembly comprising:

an anchor member including an elongated body having a proximal region terminating in a proximal end, and a distal region with a successively narrower cross-section terminating in a distal end to facilitate insertion into a hole drilled in a bone;

a driver member having a handle member and a shaft member, said shaft member having a drive element at its distal end;

means, disposed in said proximal region, for releasably engaging said driver for insertion of said anchor into the drilled hole;

at least one non-helical ridge, disposed about the exterior surface of said body, for engaging the bone after insertion to resist withdrawal of said anchor; and means, defined in said elongated body, for carrying a portion of a suture to hold the suture at a selected position in the bone.

18. The assembly of claim 17 wherein said shaft member has a projecting member thereon as said drive element and said anchor member has a socket therein, said socket and said projecting member being dimensioned to allow mating assembly of said anchor member on said shaft member.

19. The anchor of claim 18 in which said socket is narrower in cross-section along a first dimension than along another dimension.

20. The assembly of claim 17 wherein said driver member has suture fixation means thereon for securely retaining a different portion of the suture to assist attachment of said anchor member to said shaft member.

21. The assembly of claim 20 further comprising at least one groove on said shaft member in which the suture is positionable.

22. The assembly of claim 21 wherein said suture fixation means includes opposing posts and two opposed grooves are provided on said shaft member in alignment with said posts.

23. The assembly of claim 17 further comprising a guide member for limiting the dept insertion of the anchor member.

24. The assembly of claim 23 wherein said guide member comprises a hollow cylinder positionable over said shaft member.

25. The assembly of claim 23 wherein said guide member by an integral shoulder of said shaft member.

26. The assembly of claim 17 further including a suture slidably mounted within said means for carrying.

* * * * *

UNITED STATES PATENT AND TRADEMARK OFFICE
CERTIFICATE OF CORRECTION

PATENT NO. : 5,258,016
DATED : November 2, 1993
INVENTOR(S) : DiPoto, et. al.

It is certified that error appears in the above-indentified patent and that said Letters Patent is hereby corrected as shown below:

Col. 14, Line 16,

"dept" should read --depth of--

Signed and Sealed this

Eleventh Day of October, 1994

Attest:

BRUCE LEHMAN

Attesting Officer

Commissioner of Patents and Trademarks